(12) United States Patent
Kitamura et al.

(10) Patent No.: US 8,358,405 B2
(45) Date of Patent: Jan. 22, 2013

(54) MEASURING APPARATUS, AND LIQUID COLLECTING AND MEASURING SYSTEM HAVING THE SAME

(75) Inventors: Keishi Kitamura, Kyoto (JP); Takahiro Nishimoto, Kyoto (JP); Yuichi Kimura, Chiba (JP); Chie Seki, Chiba (JP); Iwao Kanno, Chiba (JP)

(73) Assignees: Shimadzu Corporation, Kyoto (JP); National Institute of Radiological Sciences, Chiba (JP)

( * ) Notice: Subject to any disclaimer, the term of this patent is extended or adjusted under 35 U.S.C. 154(b) by 363 days.

(21) Appl. No.: 12/863,968

(22) PCT Filed: Jan. 22, 2008

(86) PCT No.: PCT/JP2008/050803
§ 371 (c)(1),
(2), (4) Date: Jul. 21, 2010

(87) PCT Pub. No.: WO2009/093306
PCT Pub. Date: Jul. 30, 2009

(65) Prior Publication Data
US 2010/0294950 A1 Nov. 25, 2010

(51) Int. Cl.
*G01N 33/48* (2006.01)
(52) U.S. Cl. .......................................... 356/39
(58) Field of Classification Search .................. 356/39; 382/134
See application file for complete search history.

(56) References Cited

U.S. PATENT DOCUMENTS

| 7,943,348 B2 | 5/2011 | Cho et al. |
| 7,989,163 B2 | 8/2011 | Takahashi |
| 2006/0084174 A1* | 4/2006 | Ogawa et al. ................ 436/63 |

FOREIGN PATENT DOCUMENTS

| JP | 56-147013 A | 11/1981 |
| JP | 1-307608 A | 12/1989 |
| JP | 2004-109082 A | 4/2004 |
| JP | 2005-253466 A | 9/2005 |
| JP | 2005-300292 A | 10/2005 |

OTHER PUBLICATIONS

International Search Report for he Application No. PCT/JP2008/050803 mailed Apr. 22, 2008.
Convert. L. at al., "A Microvolumetric β Blood Counter for Pharmacokinetic PET Studies in Small Animals", IEEE Transactions on Nuclear Science, 2007, vol. 54, No. 1, pp. 1-8.
Wu, Hslao-Ming at al,, "In Vivo Quantitation of Glucose Metabolism in Mice Using Small-Animal PET and a Microfluidic Device", Journal of Nuclear Medicine, 2007, vol. 48, No. 5, pp. 837-845.
Notification of Reasons for Refusal for the Application No. 2009-550391 from Japan Patent Office mailed Feb. 28, 2012.

* cited by examiner

*Primary Examiner* — Roy M Punnoose
(74) *Attorney, Agent, or Firm* — Cheng Law Group, PLLC

(57) ABSTRACT

A blood collecting apparatus includes a main flow path and a pressure generator. The pressure generator is provided in an intermediate position of the main flow path to insert a gas as separators at designated predetermined intervals, thereby to take out blood to be measured, as separated in a time series. The blood can be taken out in minute volumes by inserting the separators consisting of the gas while feeding the blood continuously into the main flow path in this way. And consumption of the blood can be held down, and the amount of collected blood can be minimized. Since the operation to insert the separators is excellent in speed, repeated collection in a short time, i.e. frequency of blood collection, can be secured.

11 Claims, 5 Drawing Sheets

MEASURING APPARATUS, AND LIQUID COLLECTING AND MEASURING SYSTEM HAVING THE SAME

TECHNICAL FIELD

This invention relates to a measuring apparatus for collecting a liquid to be measured, as separated in a time series, and measuring light generating from a luminescent or fluorescent substance included in the collected liquid, or radiation included in the liquid, and a liquid collecting and measuring system having the same.

BACKGROUND ART

The measuring apparatus will be described taking a blood collecting apparatus which collects blood, for example. The measuring apparatus will be described taking, for example, an apparatus for counting radiation included in the blood and measuring count information such as a count of the radiation or radioactive concentration. These apparatus are used for quantitative analyses in nuclear medicine diagnosis (e.g. PET (Positron Emission Tomography), SPECT (Single Photon Emission CT) and so on), and are used especially for measurement of a radioactive concentration in arterial blood of small animals (e.g. mice, rats and so on). Conventionally, the following modes (a)-(c) are employed in the quantitative analysis of the above small animals:

(a) Manual Blood Collection

Blood delivering itself under blood pressure from the other end of a catheter inserted into a mouse artery is received in a suitable receptacle. Then, a fixed volume of the blood in the receptacle is sucked up with a volumetric pipette, and a radioactive concentration in whole blood is measured by calculating (i.e. counting) radiation in the sucked-up blood. Further, plasma is obtained by centrifugal separation of the blood remaining in the receptacle, which is similarly collected with a volumetric pipette to measure a radioactive concentration in plasma.

(b) Artery Channel β-Ray Detector

A β+ ray detector is installed in an arterial blood channel to measure a radioactive concentration in blood. β+ rays are detected with a plastic scintillator or PIN diode. In Nonpatent Document 1, for example, a diode has a long and thin shape with a length of 30 [mm], and a detectable area is increased by installing a tube containing blood along the direction of a long side, thereby to secure detection efficiency.

(c) Microfluidic Device Mode

This is a mode which, as shown in FIG. 8, leads arterial blood delivering itself under mouse blood pressure onto a microchip (device) MC. The microchip MC has, arranged thereon, one main flow path $F_M$, selectable branch flow paths $F_B$, and side flow paths $F_N$ for feeding a heparin solution H used for flow path cleaning or blood discharging, and for draining used heparin solution H and blood B. A receptacle is placed at the end of each branch flow path $F_B$, and one of the branch flow paths $F_B$ is selected by a gas pressure of argon gas Gas supplied to the microchip MC or a mechanism of the microchip MC. With one of the branch flow paths $F_B$ selected, blood B is poured in. Each of the flow paths $F_M$ and $F_B$ is formed by grooving the microchip MC in a predetermined size. It is the characteristic of the microchip MC that a minute volume of blood B is specified if a groove length or a groove area of the poured-in blood B is known. With the blood B of a predetermined volume filling the flow paths, based on the specified minute volume, the blood B sent into a predetermined receptacle (not shown) by feeding the heparin solution H under pressure. Subsequently, each of the flow paths $F_M$ and $F_B$ is cleaned with the heparin solution H to be ready for a next blood collection. The blood B in the receptacle is sucked up along with physiological saline into another receptacle, and the radiation in the blood B is counted with a well counter (see Nonpatent Document 2, for example).

[Nonpatent Document 1]
L. Convert, G. M. Brassard, J. Cadorette, D. Rouleau, E. Croteau, M. Archambault, R. Fontaine, and R. Lecomte, "A microvolumetric β blood counter for pharmacokinetic PET studies in small animals," IEEE Transactions on Nuclear Sci, vol. 54, no. 1, 2007.

[Nonpatent Document 2]
H. _M. Wu, G. Sui, C. _C. Lee, M. L. Prins, W. Ladno, H. _D. Lin, A. S. Yu, M. E. Phelps, and S. _C. Huang, "In vivo quantitation of glucose metabolism in mice using small-animal PET and a microfluidic device," J Nucl Med, vol. 48, pp. 837-845, 2007.

DISCLOSURE OF THE INVENTION

Problem to be Solved by the Invention

However, the modes (a)-(c) above have a problem with the volume of collected blood and frequency of blood collection, and a problem that it is impossible to determine accurately a hematocrit value or a radioactive concentration in blood which is count information per unit volume. Even if a minute volume of blood is specified in the mode (c), radioactivity will attenuate during the transfer to another receptacle. There is a possibility that statistical precision of the hematocrit value and the radioactive concentration in plasma which is count information per unit volume will lower as with the latter problem. The former problem will be described in detail below.

(I) Blood Volume (Volume of Collected Blood)

The body weight of a mouse is assumed to be 30 [g]. Since roughly 7.5% of the weight is blood, the total blood volume assumed is 2250 [μL]. With a loss up to about 10% of the total blood volume, the influence on the physiological condition of the mouse can be disregarded, and thus a permissible maximum volume of collected blood is 225 [μL]. The mode (a) above is a mode in which blood is once taken out in an amount corresponding at least to the specified volume, and the specified volume is sucked up therefrom. This results in a loss of a large amount of blood. Therefore, the sampling number (the number of blood samples) obtained within the permissible maximum volume of collected blood is small, and a quantitative analysis cannot be conducted fully. The mode (b) above continues pouring blood into the above-noted tube at a fixed flow rate (e.g. at least 8 [μL/min] with the condition that no coagulation takes place). Therefore, measurement time is restricted in order to be less than the permissible maximum volume of collected blood, and a prolonged quantitative analysis cannot be conducted. The mode (c) above realizes a constant volume by filling up the entire flow paths on the microchip with blood, and inhibits contamination between different times of blood collection by cleaning the entire flow paths with the heparin solution for every blood collection. Therefore, the blood that remains in locations other than constant volume portions of the minute flow rate chip is wasted at every blood collection, which increases the total amount of collected blood. Particularly, blood remaining in unused spaces such as connections to the chip is wasted at every blood collection, which is considered to increase the total amount of collected blood with every blood collection.

(II) Frequency of Blood Collection

With mice, blood collection at a maximum rate of every second is needed, considering that radioactivity variations in blood immediately after administration of a radioactive drug is more rapid than with humans. The mode (a) above is a mode in which blood is once taken out in an amount corresponding at least to the specified volume, and the specified volume is sucked up therefrom, as noted hereinbefore. Therefore, high frequency measurement is procedurally difficult. A catheter used in withdrawing blood is very thin and considering also the viscosity of blood, a very high speed cannot be expected in dripping blood from the tip end of the catheter toward a syringe for sample holding, either. Based on the above, high frequency blood collection is impossible with the mode (a). The mode (c) above once fills the blood flow paths with blood, and washes it out with a heparin solution. Since the entire flow paths on the chip (device) are filled with blood for every blood collection, the entire flow paths need to be cleaned with the heparin solution before moving on to a next blood collection as noted above. Therefore, blood or the heparin solution needs to be filled into the flow paths successively for every blood collection, which may consume time, and this is unsuitable to high-frequency blood collection.

Besides the former problem of the amount of collected blood and frequency of blood collection noted above, there is the following further problem when obtaining plasma and blood cells through centrifugal separation of the blood.

(III) Whole Blood and Plasma Radioactivity Measurement

In PET quantitative analysis, both of radioactive concentrations in whole blood and plasma are needed. Since radiation of the tube in which whole blood flows is counted in the mode (b) above, measurement of radioactivity in plasma is impossible. It is necessary to measure a radioactivity ratio of whole blood and plasma with another mouse beforehand, or collect blood separately several times during measurement, and to acquire a whole blood to plasma ratio therefrom. It is considered that, because of the low radioactivity level in mouse blood, radioactivity measurement (counting of radiation) takes time. After counting the radiation of whole blood, plasma may once be separated through centrifugal separation, and the radiation of plasma may be counted thereafter. But then, there is a chance that the radiation has already attenuated so that measurement cannot be carried out fully. In the mode (c) above, since plasma has not been separated from the blood poured into the branch flow paths $F_B$ to undergo quantitative analysis as shown in FIG. 8, plasma must be separated in a further step using another receptacle. The entire microchip must be rotated if plasma separation is carried out in the branch flow paths $F_B$. Where the structure of the microchip extends along the long side, centrifugal separation which rotates the entire microchip is difficult because of the problem of the structure forming the main flow path $F_M$.

This invention has been made having regard to the state of the art noted above, and its object is to provide a measuring apparatus and a liquid collecting and measuring system having the same, which can reduce the amount of liquid collected, secure the frequency of collection, and accurately obtain information on light or radiation per unit volume.

Means for Solving the Problem

To fulfill the above object, this invention provides the following construction.

A measuring apparatus of this invention is a measuring apparatus for measuring light generating from a luminescent or fluorescent substance included in a liquid to be measured or radiation included in the liquid to be measured, comprising (A) a detecting device for simultaneously detecting the light or the radiation in two dimensions to obtain two-dimensional image information on the light or the radiation, and (B) an information calculating device for obtaining information on the light or the radiation per unit volume based on a volume of the liquid determined from image information on a flat plate storing the liquid and having a plurality of grooves and information on the grooves grooved in the flat plate, and the two-dimensional image information on the light or the radiation obtained by the detecting device.

The measuring apparatus of this invention includes (A) a detecting device and (B) an information calculating device. Based on a volume of the liquid determined from image information on the flat plate storing the liquid and having a plurality of grooves and information on the grooves grooved in the flat plate, and two-dimensional image information on light or radiation obtained by the detecting device, the information calculating device obtains information on the light or radiation per unit volume. That is, as for the liquid already transferred to the flat plate, no variation such as a subsequent decrease occurs with the volume of the liquid derived from the image information on the flat plate and the information on the grooves grooved in the flat plate, and based on the volume of the liquid, the information on the light or radiation per unit volume is obtained. Therefore, by using the image information on the flat plate, the information on the light or radiation per unit volume can be obtained accurately, with no variation in the volume of the liquid. The detecting device can reduce the influence of photobleaching of light or attenuation of radiation by carrying out simultaneous detection in two dimensions.

In the measuring apparatus of this invention noted above, one example of the liquid to be measured is blood, and the detecting device may detect radiation included in the blood. In this case, based on the volume of the blood and the count information on the radiation obtained by the detecting device, the information calculating device can obtain count information on the radiation per unit volume accurately. The liquid may be a liquid including a fluorescent agent. In the case of a liquid including a fluorescent agent, for example, a fluorescent substance which is a fluorescent agent is included in the liquid. The measuring apparatus of this invention will measure light generating from a luminescent or fluorescent substance, thereby to obtain information on light per unit volume. It is to be noted that "luminescence" as used in this specification includes luminescence and fluorescence.

Where the liquid to be measured is blood, the detecting device counts and detects separately, as two-dimensional radiation information, the radiation included in the plasma and blood cell resulting from a plasma separation centrifuging the blood. Based on the volume of each part of the plasma and blood cell and the count information on the radiation of each part obtained by the detecting device, the information calculating device obtains count information on each part per unit volume. It is possible to determine volumes of parts of the plasma and blood cell in parallel, thereby to obtain count information on each part per unit volume in parallel (i.e. to obtain at the same time). This simultaneous calculation can extend detection time (measuring time) by the detecting device, which provides also an advantage that a low-concentration dose of radiation can be measured with high statistical accuracy.

Further, a liquid collecting and measuring system of this invention is a liquid collecting and measuring system having a liquid collecting apparatus for collecting a liquid to be measured, and a measuring apparatus for measuring light generating from a luminescent or fluorescent substance included in the liquid collected or radiation included in the liquid, comprising (A) a detecting device for simultaneously detecting the light or the radiation in two dimensions to obtain two-dimensional image information on the light or the radiation, and (B) an information calculating device for obtaining information on the light or the radiation per unit volume based on a volume of the liquid determined from image information on a flat plate storing the liquid and having a plurality of grooves and information on the grooves grooved in the flat plate, and the two-dimensional image information on the light or the radiation obtained by the detecting device.

According to the blood collecting and measuring system of this invention, as with the measuring apparatus of this invention, as for the liquid already transferred to the flat plate, no variation such as a subsequent decrease occurs with the volume of the liquid derived from the image information on the flat plate and the information on the grooves grooved in the flat plate, and based on the volume of the liquid, the information on light or radiation per unit volume is obtained. Therefore, by using the image information on the flat plate, the information on the light or the radiation per unit volume can be obtained accurately, with no variation in the volume of the liquid.

In the blood collecting and measuring system of this invention noted above, the liquid collecting apparatus included in the system is not limited to any construction as long as it collects the liquid to be measured, but preferably includes (a) a flow path and (b) an extracting device. That is, the extracting device inserts a gas or a liquid other than the above-noted liquid to be measured, as separators, at designated predetermined intervals, thereby to take out the liquid to be measured, as separated in a time series. For each liquid taken out by the extracting device, the measuring apparatus included in the system measures light generating from a luminescent or fluorescent substance included in the liquid or radiation included in the liquid to be measured. Thus, the amount of collected liquid can be reduced, and the frequency of collection can be secured. As noted with relation to the measuring apparatus of this invention, the information on light or radiation per unit volume can be obtained accurately.

In the liquid collecting and measuring system of these inventions noted above, the above flow path, preferably, is formed of what has been grooved in a predetermined size in a planar substrate. It is also preferred to include (c) an optical measuring device. For application to centrifugal separation of the liquid, (d) a flat plate and (e) a rotating device may be provided. The flat plate is the same as the flat plate which stores the liquid (to be measured), and has a plurality of grooves formed in the predetermined size. The plurality of grooves are formed to allow the liquid to be measured to circulate with respect to the flow path, and are formed to extend radially.

In carrying out such centrifugal separation, (f) an image pickup device, (g) a groove length and groove area calculating device and (h) a volume calculating device may be provided. In this case, the shade difference of the image corresponds to the image information of the flat plate in the liquid collecting and measuring system. The cross-sectional area of the grooves or the depth of the grooves corresponds to the information on the grooves in the liquid collecting and measuring system.

In the liquid collecting and measuring system of these inventions noted above, as described with relation to the measuring apparatus of this invention, one example of the liquid to be measured is blood, and the detecting device may detect the radiation included in the blood. Where the liquid to be measured is blood, as described with relation to the measuring apparatus of this invention, the detecting device counts and detects separately the radiation included in the plasma and blood cell resulting from the plasma separation centrifuging the blood. Based on the volume of each part of the plasma and blood cell and the count information on the radiation of each part obtained by the detecting device, the information calculating device may obtain the count information on each part per unit volume.

Effects of the Invention

With the measuring apparatus and liquid collecting and measuring system according to this invention, as for the liquid already transferred to the flat plate, no variation such as a subsequent decrease occurs with the volume of the liquid derived from the image information on the flat plate and the information on the grooves grooved in the flat plate, and based on the volume of the liquid, the information on light or radiation per unit volume is obtained. Therefore, by using the image information on the flat plate, the information on light or radiation per unit volume can be obtained accurately, with no variation in the volume of the liquid.

DESCRIPTION OF REFERENCES

Figure 1:
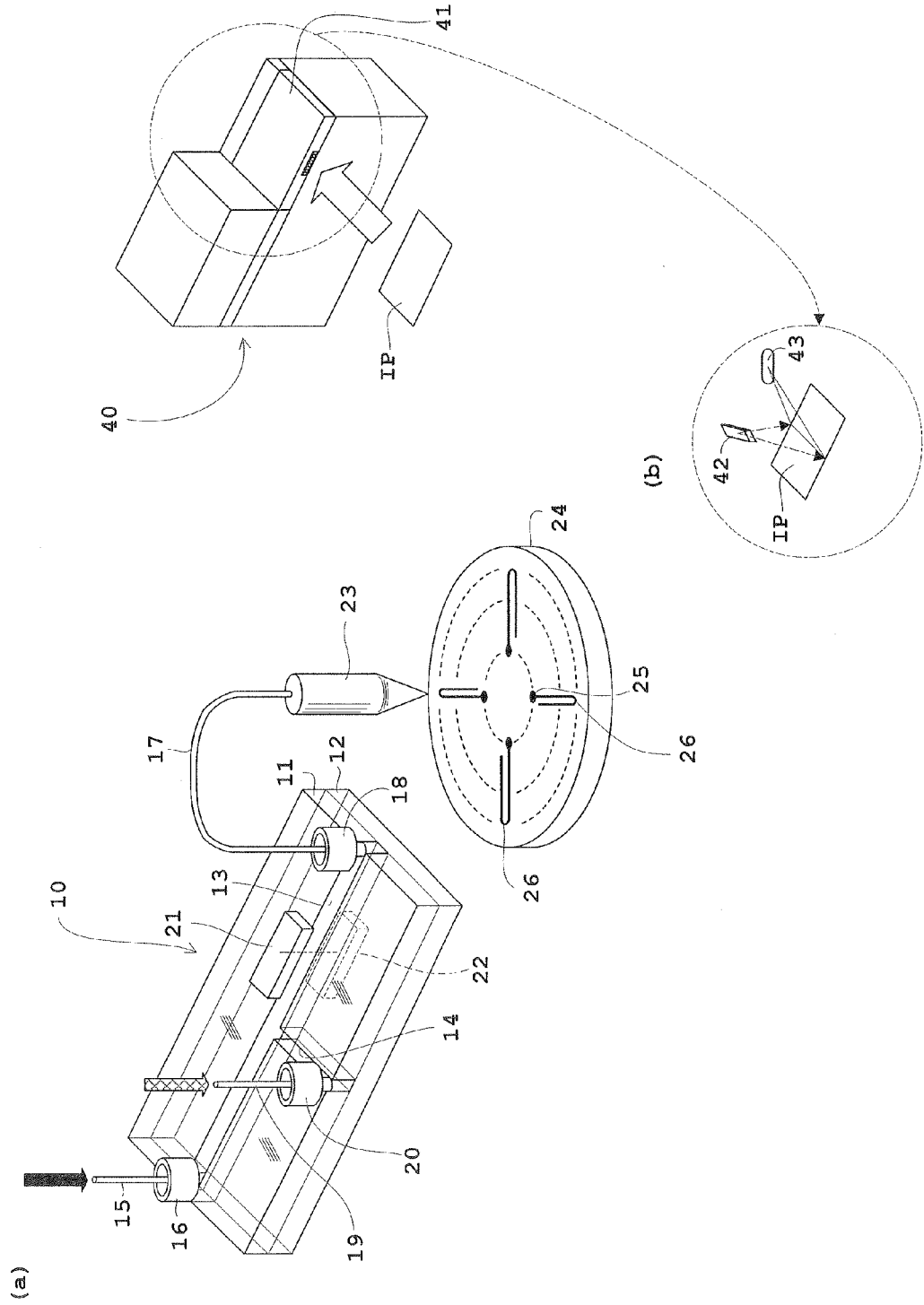
FIGS. 1 (a) and (b) are outline perspective views of a blood collecting apparatus and a measuring apparatus of a blood collecting and measuring system according to an embodiment.

10 . . . blood collecting apparatus
11 . . . glass substrate
13 . . . main flow path
21 . . . light source
22 . . . photodiodes
24 . . . disk (CD well)
26 . . . grooves
30 . . . pressure generator
31 . . . rotating unit
32 . . . image pickup unit
34 . . . groove length and groove area calculating unit
35 . . . volume calculating unit
40 . . . measuring apparatus
41 . . . reading unit
44 . . . information calculating unit
IP . . . imaging plate

EMBODIMENT

Figure 2:
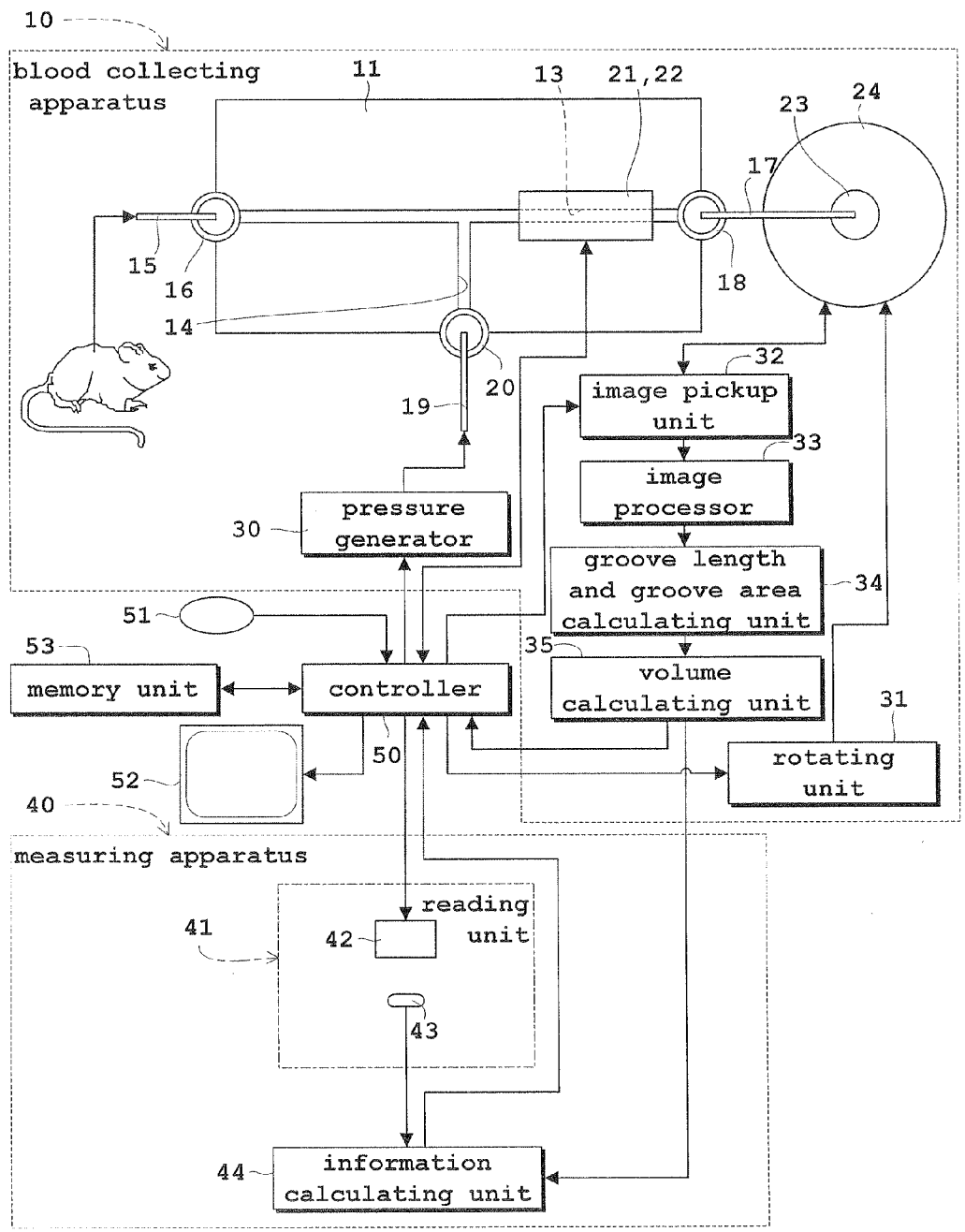
FIG. 2 is a block diagram of the blood collecting apparatus and measuring apparatus of the blood collecting and measuring system according to the embodiment.

An embodiment of this invention will be described hereinafter with reference to the drawings. FIG. 1 is an outline perspective view of a blood collecting apparatus and a measuring apparatus of a blood collecting and measuring system according to the embodiment. FIG. 2 is a block diagram of the blood collecting apparatus and measuring apparatus of the blood collecting and measuring system according to the embodiment. This embodiment will be described, taking blood as an example of liquid to be measured, taking a blood collecting and measuring system as an example of liquid collecting and measuring system, and taking a blood collecting apparatus as an example of liquid collecting apparatus.

The blood collecting and measuring system according to this embodiment, as shown in FIG. 1, includes a blood collecting apparatus 10 for collecting blood to be measured, as separated in a time series, and a measuring apparatus 40 for measuring radiation (e.g. β-rays, γ-rays or the like) included in the collected blood. In this embodiment, blood is collected after introducing a radioactive drug into the body of a mouse, and radiation included in the blood is measured. Further, a plasma separation is carried out, and each of the radiations included in the plasma and blood cell resulting from the plasma separation is measured. The blood collecting apparatus 10 corresponds to the liquid collecting apparatus in this invention. The measuring apparatus 40 corresponds to the measuring apparatus in this invention.

The blood collecting apparatus 10 has a microchip formed of two glass substrates 11 and 12, one superposed on the other. The upper glass substrate 11 is grooved in a T-shape of a predetermined size, and grooves resulting from the grooving form a main flow path 13 and a side path 14, respectively. This done, the upper glass substrate 11 and glass substrate 12 are bonded together, with the groove-forming face placed inside. That is, the main flow path 13 and side path 14 refer to pipe conduit portions grooved in the predetermined size in the planar glass substrate 11, and provided with the glass substrate 12. The glass substrate 11 corresponds to the substrate in this invention. The main flow path 13 corresponds to the flow path in this invention. Here, the material for the blood collecting apparatus 10 is not limited to glass, but may be any optically transparent material such as acrylic, polycarbonate, COP (cycloolefin polymer) or the like. When the main flow path 13 and side path 14 are formed as open flow paths rather than the pipe conduits, the upper glass substrate 11 and glass substrate 12 may be bonded together, with the groove-forming face placed outside.

A catheter 15 is disposed at a blood inlet of the main flow path 13, and the main flow path 13 and catheter 15 are connected through a connector 16. The microchip formed of the glass substrates 11 and 12 is set very close to the mouse, and the catheter 15 which is used for withdrawing blood is connected by the above connector 16, thereby to prevent a wasteful outflow of blood. In this way, blood is continuously fed into the main flow path 13 through the catheter 15. Conversely, blood piping 17 is disposed at a blood outlet of the main flow path 13, and the main flow path 13 and blood piping 17 are connected through a connector 18. On the other hand, bubble piping 19 is disposed at an inlet of the side path 14, and the side path 14 and bubble piping 19 are connected through a connector 20. An outlet of the side path 14 is connected for communication with the main flow path 13, whereby bubbles are fed into the main flow path 13 through the side path 14.

A function may be provided as necessary to clean the flow paths by pouring a heparin solution into the flow passages of the main flow path 13 and side path 14. Further, in order to prevent an occurrence of blood coagulation in the flow passages of the main flow path 13 and side path 14, it is preferable to carry out a process of actually introducing an anticoagulant, or applying an anticoagulant to inner surfaces of the flow paths to coat the latter.

A light source 21 and photodiodes 22 are opposed to each other across the main flow path 13. Light is emitted from the light source 21 to the blood flowing through the main flow path 13, and the photodiodes 22 detect light-shielding by the blood, thereby to measuring length information on the blood described hereinafter while optically monitoring the blood. The light source 21 and photodiodes 22 correspond to the optical measuring device in this invention.

On the other hand, a dispenser 23 is connected downstream of the above blood piping 17. A disk (also called "CD well") 24 is disposed for receiving and storing the blood dripping from this dispenser 23. The disk 24 has a plurality of openings 25 arranged centrally and radially thereof for receiving the dripping blood. The disk 24 is grooved, as is the above glass substrate 11, and a plurality of U-shaped grooves 26 are formed radially by the grooving. Each U-shaped groove 26 is connected in a one-to-one relationship to one outer end of the above opening 25, and each U-shaped groove 26 is formed to extend radially of the disk 24. With the dispenser 23 interposed in this way, the disk 24 is formed capable of circulating blood with respect to the main flow path 13. The disk 24 corresponds to the flat plate in this invention.

On the other hand, the measuring apparatus 40 has a reading unit 41. This reading unit 41 has a cover for inserting an exposed imaging plate IP, and detects $\beta^+$ rays included in the blood by reading excited light from the imaging plate IP. Specifically, as shown in FIG. 1 (b), the reading unit 41 has a laser light source 42 and a photomultiplier tube 43. $\beta^+$ rays are simultaneously detected in two dimensions by emitting laser from the laser light source 42 to the imaging plate IP, with the photomultiplier tube 43 converting to and multiplying electrons, the light excited by the laser emission to the imaging plate IP. The imaging plate IP and reading unit 41 correspond to the detecting device in this invention.

Next, the block diagram of the blood collecting apparatus 10 and measuring apparatus 40 will be described. The blood collecting apparatus 10 includes, besides the components described hereinbefore such as the glass substrate 11, main flow path 13 and disk 24, and as shown in FIG. 2, a pressure generator 30, a rotating unit 31, an image pickup unit 32, an image processor 33, a groove length and groove area calculating unit 34 and a volume calculating unit 35. The measuring apparatus 40 includes an information calculating unit 44 besides the reading unit 41 described above. In addition, the blood collecting apparatus 10 and measuring apparatus 40 share a controller 50, an input unit 51, an output unit 52 and a memory unit 53. The pressure generator 30 corresponds to the extracting device in this invention. The rotating unit 31 corresponds to the rotating device in this invention. The image pickup unit 32 corresponds to the image pickup device in this invention. The groove length and groove area calculating unit 34 corresponds to the groove length and groove area calculating device in this invention. The volume calculating unit 35 corresponds to the volume calculating device in this invention. The information calculating unit 44 corresponds to the information calculating device in this invention.

The pressure generator 30 takes out blood to be measured, as separated in a time series, by controlling the pressure of a gas (e.g. air, argon or the like), feeding the gas into the main flow path 13 through the side path 14, and introducing the gas as bubbles at specified predetermined intervals. That is, the bubbles perform a function as the separators in this invention. Although a gas is used as the separators, instead of being limited to the gas, a liquid other than the liquid to be measured may be used as the separators as long as this liquid has little or no chance of mixing with the liquid to be measured (blood in this embodiment). Where the liquid to be measured is blood as in this embodiment, a liquid represented by mineral oil, fluorine-based oil or the like, which does not mix with blood, may be used as the separators.

The rotating unit 31 includes a motor and a turntable not shown. Rotation of the motor rotates the turntable, to rotate the disk 24 placed on the turntable. The centrifugal force of the disk 24 by this rotating unit 31 is used to centrifuge the liquid to be measured (blood in this embodiment). Where the liquid to be measured is blood as in this embodiment, the centrifugal force of the disk 24 by the rotating unit 31 is used to carry out a plasma separation to centrifuge the blood into plasma and blood cell.

The image pickup unit 32 picks up an image of the disk 24. In this embodiment, a flat bed scanner is employed as the image pickup unit 32, which includes a linear light source (not shown) having a length at least corresponding to the diameter of the disk 24, and a linear photodiode array (i.e. a line sensor) (not shown) opposed to the light source across the disk 24. The flat bed scanner scans over the disk 24 to pick up an image of the disk 24, thereby acquiring the image of the disk 24. The image processor 33 carries out various processes on the image of the disk 24 obtained by the image pickup unit 32. For example, a lag correction, a dynamic range conversion and so on may be carried out.

The groove length and groove area calculating unit 34 determines a groove length or a groove area of each part of the centrifuged liquid (blood in this embodiment), based on shade differences of the image picked up by the image pickup unit 32, in the U-shaped grooves 26 (see FIG. 1) grooved in the disk 24. Where the liquid to be measured is blood as in this embodiment, the groove length and groove area calculating unit 34 determines a groove length or a groove area of each part of the plasma and blood cell having undergone the plasma separation.

The volume calculating unit 35 determines a volume of each part based on the groove length of each part of the liquid (blood in this embodiment) determined by the groove length and groove area calculating unit 34 and a cross-sectional area of the grooves 26 (see FIG. 1), or based on the groove area of each part of the liquid (blood) determined by the groove length and groove area calculating unit 34 and a depth of the grooves 26 (see FIG. 1). Where the liquid to be measured is blood as in this embodiment, the volume calculating unit 35 determines a volume of each part based on the groove length of each part of the plasma and blood cell determined by the groove length and groove area calculating unit 34 and the cross-sectional area of the grooves 26, or based on the groove area of each part of the plasma and blood cell determined by the groove length and groove area calculating unit 34 and the depth of the grooves 26.

The information calculating unit 44 obtains count information on $\beta^+$ rays per unit volume based on the volume of the liquid (blood in this embodiment) determined by the volume calculating unit 35 and count information on $\beta^+$ rays obtained by the imaging plate IP and reading unit 41. In this embodiment, the count information on radiation is a count of $\beta^+$ rays (the unit being [Bq]), and the count information on radiation per unit volume is a radioactive concentration in blood of $\beta^+$ rays (the unit being [Bq/μL]).

The controller 50 carries out overall control of the components constituting the blood collecting apparatus 10 and measuring apparatus 40. The controller 50 is formed of a central processing unit (CPU) and others. The input unit 51 makes inputs to the controller 50. For example, the input unit 51 feeds data and commands inputted by the operator to the controller 50. The input unit 51 has a pointing device represented by a mouse, keyboard, joystick, trackball and/or touch panel. The output unit 52 outputs various data fed thereto through the controller 50. The output unit 52 is formed of a display represented by a monitor, and/or a printer.

The memory unit 53 is for writing and storing various data fed thereto through the controller 50. The memory unit 53 is formed of storage media represented by a ROM (Read-only Memory), a RAM (Random-Access Memory) and so on. In this embodiment, intervals of the blood detected by the photodiodes 22, various data processed by the image processor 33, the groove length or groove area of each part of plasma and blood cell determined by the groove length and groove area calculating unit 34, the volume of each part determined by the volume calculating unit 35, and the radioactive concentration in blood determined by the information calculating unit 44, are written and stored in the RAM, and are read from the RAM as necessary. The ROM stores programs for carrying out various types of quantitative analysis. The controller 50 executes the programs to carry out the types of quantitative analysis corresponding to the programs, respectively.

The image processor 33, groove length and the groove area calculating unit 34, volume calculating unit 35 and information calculating unit 44 are realized by the controller 50 executing, for example, the programs stored in the ROM of the storage medium represented by the above memory unit 53, or commands inputted with the pointing device represented by the input unit 51.

Figure 3:
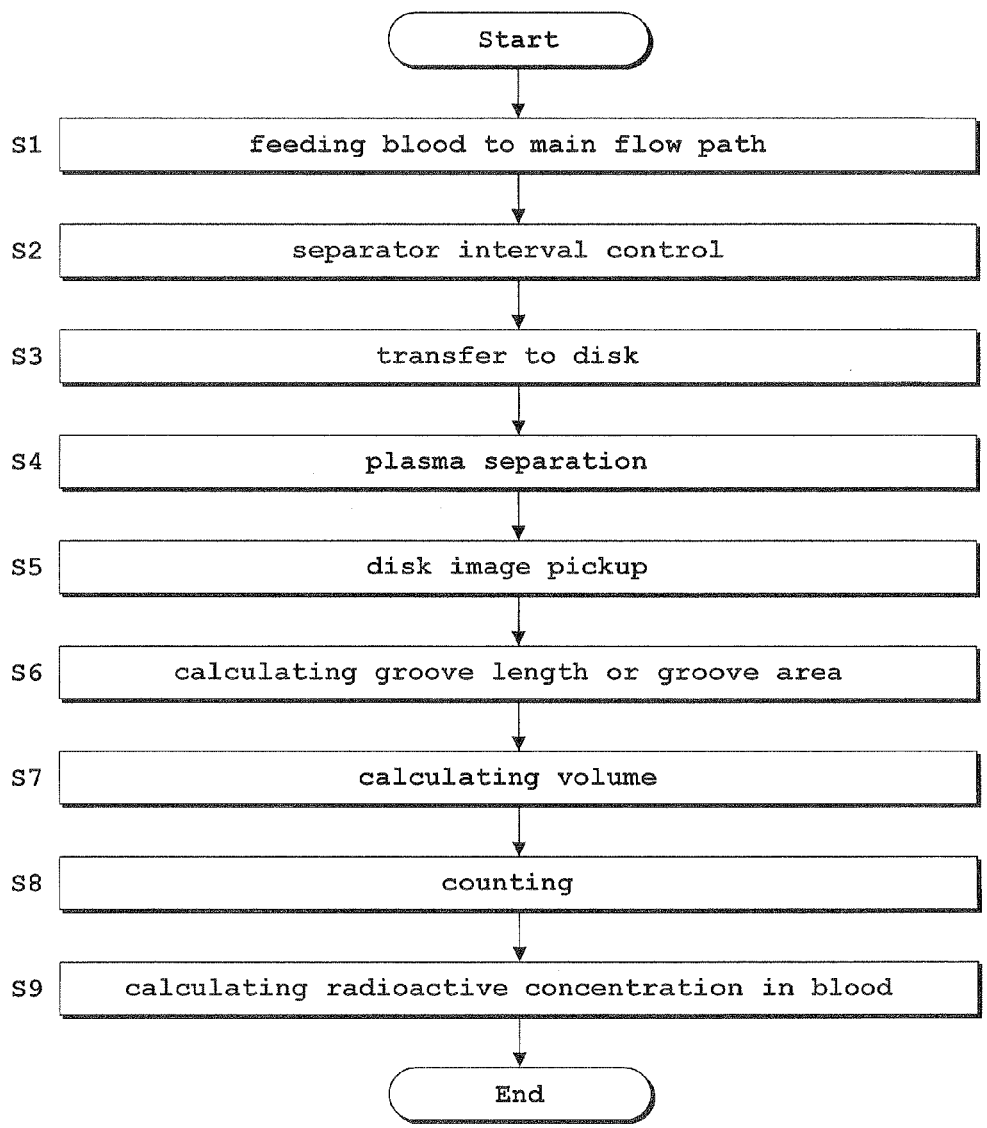
FIG. 3 is a flow chart showing a sequence of processes relating to a series of quantitative analyses according to the embodiment.
Figure 4:
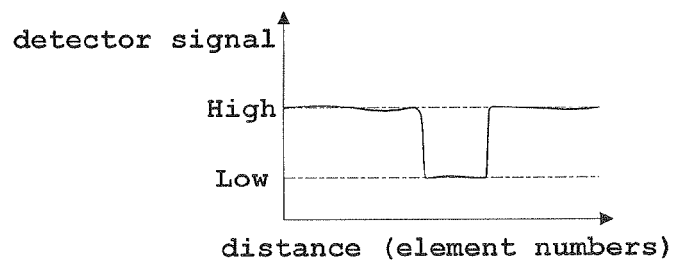
FIG. 4 is a view schematically showing output of detector signals.
Figure 5:
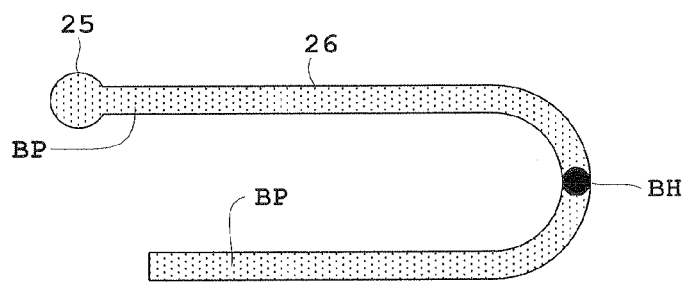
FIG. 5 is a view schematically showing conditions of plasma and blood cell resulting from a plasma separation.
Figure 6:
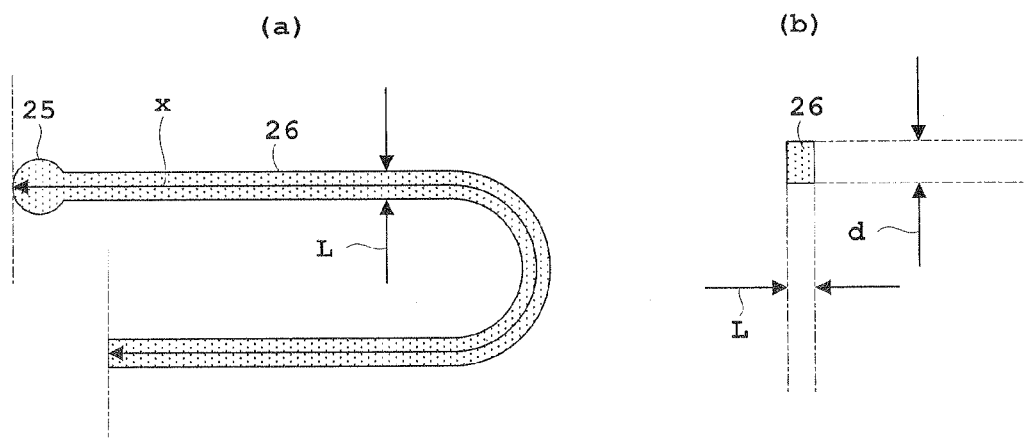
FIG. 6 (a) is an outline plan view of a groove in a disk, and (b) is an outline sectional view of the groove in the disk.
Figure 7:
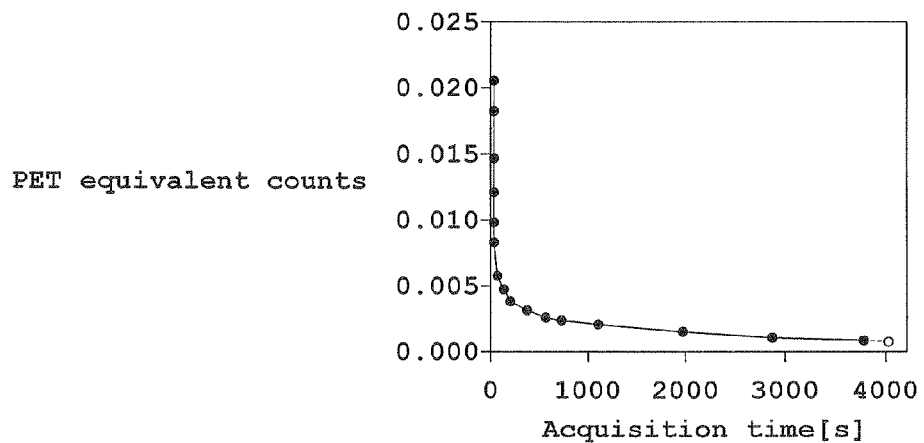
FIG. 7 is a graph of a blood radioactive concentration curve.
Figure 8:
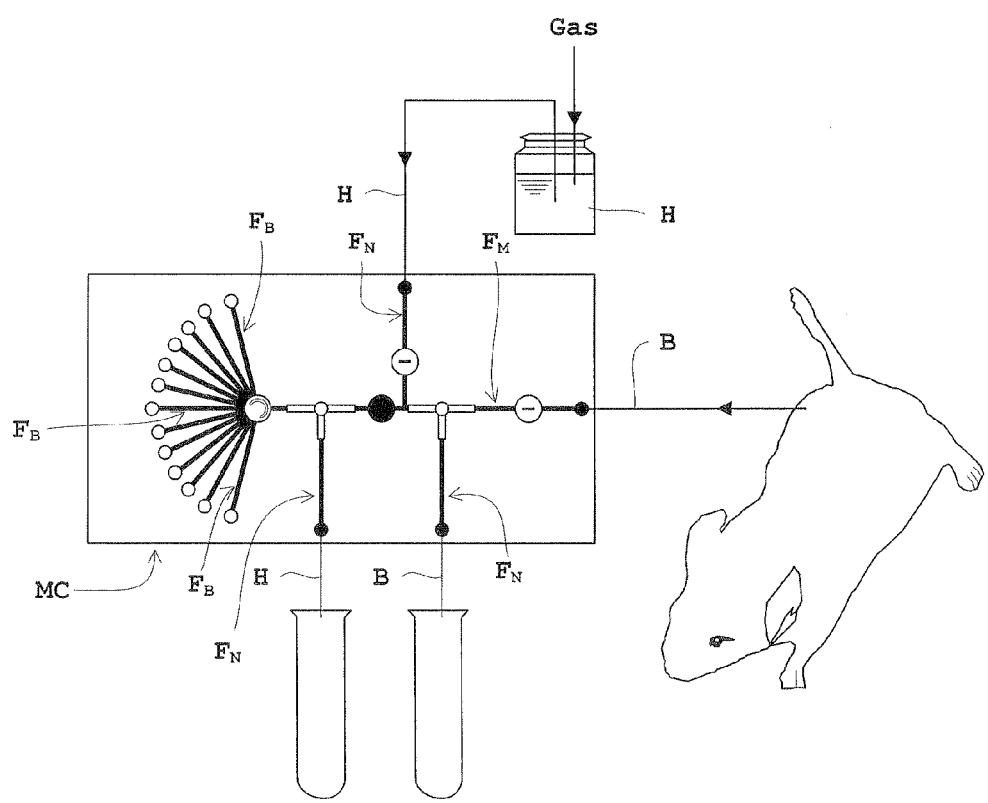
FIG. 8 is a plan view showing an entire microchip construction at the time of a conventional microfluidic device mode.

Next, processes relating to a series of quantitative analyses will be described with reference to FIGS. 3-7. FIG. 3 is a flow chart showing a sequence of processes relating to a series of quantitative analyses according to the embodiment. FIG. 4 is a view schematically showing output of detector signals. FIG. 5 is a view schematically showing conditions of plasma and blood cell resulting from a plasma separation. FIG. 6 (a) is an outline plan view of a groove in the disk. FIG. 6 (b) is an outline sectional view of the groove in the disk. FIG. 7 is a graph of a blood radioactive concentration curve.

(Step S1) Feeding Blood to Main Flow Path

Blood is continuously fed into the main flow path 13 by inserting the catheter 15 (see FIG. 1) into a mouse artery, and directing arterial blood delivering itself under mouse blood pressure to the main flow path 13 (seeing FIGS. 1 and 2) through the catheter 15. As noted hereinbefore, in order to prevent an occurrence of blood coagulation in the flow paths, it is preferable to feed the blood after introducing an anticoagulant, or performing coating treatment by applying an anticoagulant to inner surfaces of the main flow path 13 and side path 14 (see FIGS. 1 and 2).

(Step S2) Separator Interval Control

When blood is not flowing through the main flow path 13 (see FIGS. 1 and 2), the light emitted from the light source 21 (see FIGS. 1 and 2) falls on the photodiodes 22 (see FIGS. 1 and 2) opposed to the light source 21 across the main flow path 13. Therefore, as shown in FIG. 4, a detector signal having undergone a photoelectric conversion by the photodiodes 22 is outputted at High level from the photodiodes 22. Conversely, when blood is flowing through the main flow path 13, the light emitted from the light source 21 is blocked and shielded by the blood. Since the light does not fall on the photodiodes 22, as shown in FIG. 4, the detector signal is outputted at Low level from the photodiodes 22. With the photodiodes 22 detecting the light-shielding by the blood, length information on the blood is measured while optically monitoring the blood. Based on the measurement result by the photodiodes 22, the controller 50 (see FIG. 2) controls the volume of the blood to be taken out by the pressure generator 30 (see FIG. 2) by controlling intervals of the separators (i.e. bubbles in this embodiment).

Specifically, where the light source 21 and photodiodes 22 (see FIGS. 1 and 2) form a linear optical system (for example, the light source 21 is a linear light source extending along the longitudinal direction of the main flow path 13, and a linear photodiode array formed of the plurality of photodiodes 22 arranged along the same direction), as shown in FIG. 4, outputs of the detector signal relative to distance (element numbers corresponding to the respective photodiodes 22) are obtained from detections by the respective photodiodes 22. At this time, an interval where the detector signal is at Low level is a length where the blood is flowing continuously, and an interval where the detector signal is at High level is a length of a separator between blood and blood. Since the main flow path 13 is formed by grooving in a predetermined size, a volume of the blood to be taken out is derived from this blood interval (i.e. the separator length). That is, a volume of the blood to be taken out can be determined by multiplying the blood interval by the cross-sectional area of the main flow path 13.

Based on the length information on the blood obtained in this way, the controller 30 (see FIG. 2) controls pressure regulation to the pressure generator 30, and the timing of feeding the gas to the main flow path 13 (see FIGS. 1 and 2) through the side path 14 (see FIGS. 1 and 2), in order to control the volume of the blood to be taken out by the pressure generator 30 (see FIG. 2). And the intervals of the separators (bubbles) are thereby controlled to control the volume of the blood to be taken out.

When taking out blood by a single shot where there are few separators to feed (e.g. two separators to feed), an interval between the adjoining separators, i.e. an interval of the blood to be taken out, may be controlled. When taking out blood continuously where there are many separators to feed (e.g. the separators are fed continuously with fixed timing), intervals of the separators may be controlled as above. When the flow velocity of blood is slow, or when blood is taken out by a single shot as above, the volume of blood to be taken out may be controlled by controlling directly space intervals (intervals of length) of the blood, or the space intervals (intervals of length) of the separators. When the flow velocity of blood is fast or when blood is taken out continuously as above, the volume of blood to be taken out may be controlled by controlling time intervals of the separators (cycle of the separator feeding timing) as above.

(Step S3) Transfer to Disk

Very small amounts of blood taken out in step S2 are fed into the dispenser 23 (see FIGS. 1 and 2) through the blood piping 17 (see FIGS. 1 and 2). The dispenser 23 drips each very small amount of the taken-out blood to an opening 25 (see FIG. 1) of the disk (CD well) 24 (see FIGS. 1 and 2). By this dripping, the very small amounts of the taken-out blood are transferred to the disk 24. The openings 25 and grooves 26 (see FIG. 2) are formed in the disk 24, and are used, in a number at least corresponding to the number of times of blood collection (i.e. the number of collected blood samples).

At the time of this dripping, where blood viscosity and the wettability of the blood and the surfaces it contacts are high, part of the collected blood could remain in or adjacent the main flow path 13 (see FIGS. 1 and 2). It is therefore preferable to guarantee dripping of the entire blood by carrying out water-repellent treatment of surfaces contacted by the blood, such as inner surfaces of the main flow path, a nozzle tip of the dispenser 23 (see FIGS. 1 and 2) and so on. It is also preferable to allow all the dripped blood to be drawn into the grooves 26 of the disk 24 (see FIG. 1) by carrying out hydrophilic treatment of the openings 25 (see FIG. 1) of the disk 24 (see FIGS. 1 and 2). However, the volume of blood has been measured and determined by the image pickup unit 32, groove length and groove area calculating unit 34 and volume calculating unit 35 (see FIG. 2 for all), and no problem is posed by remnant part, if any.

(Step S4) Plasma Separation

After the blood is transferred to the disk 24 (see FIGS. 1 and 2) in step S3, the controller 50 (see FIG. 2) controls the rotating unit 31 (see FIG. 2) to rotate the disk 24 and carry out plasma separation for dividing into plasma and blood cell. As noted hereinbefore, the openings 25 (see FIG. 1) are open at one outer end thereof to be connected in a one-to-one relationship to the grooves 26 (see FIG. 1), thereby to carry out separation of the blood smoothly at the time of plasma separation. The grooves 26, because they are U-shaped, prevent blood cell at the time of plasma separation from escaping out of the disk 24 under centrifugal force, and cause blood cell BH to precipitate, after the plasma separation, at the bottom of the U-shape as shown in FIG. 5. Reference BP in FIG. 5 denotes plasma. It is preferable to close the openings 25 for standby in order to prevent blood clotting during a standby time before the plasma separation. As noted in connection with the flow paths, it is preferable to apply an anticoagulant or introduce the anticoagulant to the interiors of the openings 25 and grooves 26 to prevent blood clotting.

(Step S5) Disk Image Pickup

The image pickup unit 32 (see FIG. 2) picks up an image of the plasma and blood cell having undergone the plasma separation for each disk 24 (see FIGS. 1 and 2). With the flat bed scanner acting as the image pickup unit 32, for example, scanning over the disk 24, the photodiode array of the flat bed scanner acquires an optical image of the disk 24 with the plasma and blood cell having undergone the plasma separation, and image pickup is carried out by acquiring the optical image as image of the disk 24. Then, the image processor 33 (see FIG. 2) carries out various processes on the image of the disk 24. The image pickup unit 32 is not limited to the type that picks up images optically, but may pick up images by detecting emitted radiation, for example.

(Step S6) Calculating Groove Length or Groove Area

With the linear light source of the above flat bed scanner emitting light, an absorbance difference results in a shade difference appearing on the image of the plasma and blood cell, rendering them easily discernible on the image. Based on the shade difference (i.e. absorbance difference) of the image of the grooves 26 (see FIG. 1) of the disk 24 (see FIGS. 1 and 2) picked up by the image pickup unit 32 (see FIG. 2), the groove length and groove area calculating unit 34 obtains a groove length or a groove area of each part of the plasma and blood cell. The groove length or groove area of each part of the plasma and blood cell is obtained by converting the number of one-dimensional pixels with the shade difference into the groove length, or by converting the number of two-dimensional pixels into the groove area.

(Step S7) Calculating Volume

Based on the groove length of each part of the plasma and blood cell obtained by the groove length and groove area calculating unit 34 (see FIG. 2) and the cross-sectional area of the grooves 26 (see FIG. 1), or based on the groove area of each part of the plasma and blood cell obtained by the groove length and groove area calculating unit 34 and the depth of the grooves 26, the volume calculating unit 35 (see FIG. 2) obtained a volume of each part.

As shown in the plan view of FIG. 6 (a), the length in the longitudinal direction of groove 26 (including opening 25), i.e. the groove length, is assumed to be x. As shown in the sectional view of FIG. 6 (b), where the groove has a rectangular section, the depth of groove 26 is assumed to be d. As shown in FIGS. 6 (a) and 6 (b), the length in the transverse direction of groove 26, i.e. groove width, is assumed to be L. Then, when groove length x is obtained in step S6, since the cross-sectional area of groove 26 is expressed by depth d of groove 26×groove width L, volume V can be derived from V=x×d×L. Conversely, when the groove area is obtained in step S6, since the groove area is expressed by groove length x×groove width L and the depth of the groove is d, volume V can be derived similarly from V=x×d×L. The volume of plasma is assumed to be $V_p$, and the volume of blood cell to be $V_h$.

(Step S8) Counting

Each disk 24 with the plasma and blood cell having undergone the plasma separation (refer to FIGS. 1 and 2) is stored as a sample in an opened cassette not shown, the imaging plate IP (see FIG. 1) is stored thereon, and the cassette is closed. The disk 24 is taken out of the cassette after a fixed time, and the imaging plate IP is irradiated with light for exposure. Through this exposure, electrons are captured by lattice defects of a fluorescent substance (not shown) of the imaging plate IP due to the ionizing power of $\beta^+$ rays included in the blood. The exposed imaging plate IP is taken out of the cassette, and is inserted in the cover of the reading unit 41 (see FIGS. 1 and 2) of the measuring apparatus 40 (see FIGS. 1 and 2).

Laser is emitted from the laser light source 42 (see FIGS. 1 and 2) of the reading unit 41 (see FIGS. 1 and 2) to the imaging plate IP (see FIG. 1). By this irradiation, the captured electrons are excited to be conductors to recombine with holes, and are excited as light from the fluorescent substance. The photomultiplier tube 43 (see FIGS. 1 and 2) converts into electrons and multiplies the light excited by the laser irradiation of this imaging plate IP, thereby simultaneously detecting in two dimensions and counting as electrical pulses. After the emission from the laser light source 42 to the imaging plate IP, the captured electrons are eliminated for reuse by emitting light from a light source for elimination (not shown) to the imaging plate IP.

(Step S9) Calculating Radioactive Concentration in Blood

Based on volume $V_p$ of the plasma and volume $V_h$, of the blood cell obtained by the volume calculating unit 35 (see FIG. 2), and count information on $\beta^+$ rays obtained by the imaging plate IP and reading unit 41, the information calculating unit 44 (see FIG. 2) determines a radioactive concentration in the blood which is count information on $\beta^+$ rays per unit volume.

The image of the disk 24 picked up by the image pickup unit 32 (see FIG. 2) and a distribution image of $\beta^+$ rays which is the count information obtained by the imaging plate IP and reading unit 41 are superimposed together, to match the plasma in the image of the disk 24 and the plasma in the distribution image of $\beta^+$ rays, and to match the blood cell in the image of the disk 24 and the blood cell in the distribution image of $\beta^+$ rays. Then, a radioactive concentration in blood of each part is determined by dividing the count of each part by the volume of each part. Assuming that the count in the plasma is $A_p$ and the count in the blood cell is $A_h$, radioactive concentration in blood $A_p/V_p$ in the plasma is calculated, and radioactive concentration in blood $A_h/V_h$ in the blood cell is calculated. In this case, the output value of the imaging plate IP and reading unit 41 is corrected beforehand with a known dose of radiation.

A graph of a radioactive concentration curve in blood is obtained finally as shown in FIG. 7 by rearranging results of the radioactive concentration in blood according to extraction time. The horizontal axis in FIG. 7 is extraction time, i.e. acquisition time (written "Acquisition time" in FIG. 7), while the vertical axis in FIG. 7 is the radioactive concentration in blood (written "PET equivalent counts" in FIG. 7). Thus, the volume of the extracted blood is determined by the cross-sectional area of grooves 26 (see FIGS. 1 and 2) of the disk 24 (see FIGS. 1 and 2) and image pickup accuracy of the image pickup unit 32 (see FIG. 2). The counting accuracy (statistical accuracy) of the radiation is determined by the exposure time to the imaging plate IP. Considering attenuation of the radiation and a required sampling number, a plurality of disks 24 may be made available and exposed successively with the imaging plate IP to pick up images.

The blood collecting apparatus 10 according to this embodiment includes (a) a flow path (main flow path 13 in this embodiment) and (b) an extracting device (pressure generator 30 in this embodiment). The extracting device (pressure generator 30) is provided in an intermediate position of the flow path (main flow path 13) to insert, as separators at designated predetermined intervals, a gas (air, argon or the like in this embodiment) or a liquid (mineral oil, fluorine-based oil or the like where the liquid to be measured is blood) other than the above-noted liquid to be measured (blood in this embodiment), thereby to take out the liquid (blood) to be measured, as separated in a time series. The liquid (blood) can be taken out in minute volumes of about 1 [μL], for example, by inserting the separators consisting of the gas or liquid while feeding the above liquid (blood) continuously into the flow path (main flow path 13) in this way. And consumption of the liquid (blood) to be measured accompanying a cleaning liquid (heparin solution in the case of blood collection) for every collection as in the prior art can be held down, and the amount of collected liquid (the quantity of collected blood in this embodiment) can be minimized. Since the operation to insert the separators is excellent in speed, repeated collection in a short time, i.e. frequency of collection (blood collection in this embodiment), can be secured. As a result, the amount of collected liquid (the quantity of collected blood) can be reduced, and the frequency of collection (blood collection) can be secured.

In this embodiment, the main flow path 13, preferably, is formed of what has been grooved in a predetermined size in the planar glass substrate 11. That is, with grooving in the predetermined size, if a groove length or a groove area of the liquid (blood in this embodiment) fed into the main flow path 13 is known, a volume of the liquid (blood) fed into the main flow path 13 can be specified based on the cross-sectional area of the groove or the depth of the groove formed by grooving in the predetermined size.

In this embodiment, the blood collecting apparatus 10, preferably, includes (c) an optical measuring device (light source 21 and photodiodes 22 in this embodiment). Specifically, the above optical measuring device (light source 21 and photodiodes 22) measures length information on the liquid (blood) while optically monitoring the liquid to be measured (blood in this embodiment blood) flowing through the flow path (main flow path 13 in this embodiment). The volume of the liquid (blood) to be taken out by the above extracting device (pressure generator 30 in this embodiment) is controlled by controlling the intervals of the separators based on a result of measurement by the optical measuring device (light source 21 and photodiodes 22). Thus, the flow rate of the liquid (blood), and thus the volume of the liquid (blood), can be controlled by the intervals of the separators, and the amount of collected liquid (the amount of collected blood) can be minimized.

This embodiment is applied to centrifugal separation of the liquid. That is, (d) a flat plate (disk 24 in this embodiment) and (e) a rotating device (rotating unit 31 in this embodiment) are provided, the flat plate (disk 24) has a plurality of grooves formed to allow the liquid to be measured to circulate with respect to the flow path (main flow path 13 in this embodiment) (to allow circulation with the dispenser 23 interposed) and formed radially, and the rotating device (rotating unit 31) rotates the flat plate (disk 24). It is possible to centrifuge the liquid using a centrifugal force of the flat plate (disk 24) by the rotating device (rotating unit 31). Where the liquid is blood as in this embodiment, it is possible to centrifuge the blood by using the centrifugal force of the flat plate (disk 24) by the rotating device (rotating unit 31), to effect plasma separation to divide into plasma and blood cell.

In carrying out such centrifugal separation, different parts of the centrifuged liquid (plasma and blood cell where the liquid is blood as in this embodiment) exist as divided. The parts of the centrifuged liquid (plasma and blood cell) are different from each other in light absorbance or radioactive concentration. Using the different point, an image of the flat plate (disk 24 in this embodiment) is picked up, and using the result of the image pickup, the volume of each part is determined with increased accuracy. Specifically, (f) an image pickup device (image pickup unit 32 in this embodiment), (g) a groove length and the groove area calculating device (groove length and groove area calculating 34 in this embodiment) and (h) a volume calculating device (volume calculating unit 35 in this embodiment) are provided, and the image pickup device (image pickup unit 32) picks up an image of the flat plate (disk 24 in this embodiment).

Particularly where the liquid is blood as in this embodiment, the difference in absorbance or radioactive concentration results in the plasma and blood cell appearing as a shade difference on the image picked up, rendering them easily discernible on the image. Based on the shade difference (i.e. difference in absorbance or radioactive concentration) of the image of the grooves 26 grooved in the flat plate (disk 24 in this embodiment) picked up by the image pickup device (image pickup unit 32), the groove length and groove area calculating device (groove length and groove area calculating unit 34) obtains a groove length or a groove area of each part of the centrifuged liquid (each part of the plasma and blood cell in this embodiment). Based on the groove length of each part of the liquid (each part of the plasma and blood cell) obtained by the groove length and groove area calculating device (groove length and groove area calculating unit 34) and the cross-sectional area of the grooves 26, or based on the groove area of each part of the liquid (each part of the plasma and blood cell) obtained by the groove length and groove area calculating device (groove length and groove area calculating unit 34) and the depth of the grooves 26, the volume calculating device (volume calculating unit 35) obtains a volume of each part noted above (each part of the plasma and blood cell). That is, once the groove length or groove area of each part of the liquid (each part of the plasma and blood cell) is obtained by the groove length and groove area calculating device (groove length and groove area calculating unit 34), the volume of each part (each part of the plasma and blood cell) can be obtained based on the cross-sectional area of grooves 26 or the depth of grooves 26.

A variation such as a decrease in the volume of the liquid (blood) is conceivable in that the liquid (blood in this embodiment) specified in the flow path (main flow path 13 in this embodiment) located upstream of the flat plate (disk 24 in this embodiment) is transferred to the flat plate (disk 24). However, the volume of each part (each part of the plasma and blood cell) can be determined with increased accuracy since the volume of each part of the liquid (each part of the plasma and blood cell in this embodiment) stored in the flat plate (disk 24) is determined again by using the image information (shade difference of the image) on the flat plate (disk 24) picked up by the image pickup device (image pickup unit 32 in this embodiment).

This embodiment is described taking blood as an example of the liquid to be measured. Therefore, the liquid collecting apparatus is an apparatus for collecting blood, i.e. the blood collecting apparatus 10.

The measuring apparatus 40 according to this embodiment includes (A) a detecting device (imaging plate IP and reading unit 41 in this embodiment) and (B) an information calculating device (information calculating unit 44 in this embodiment). Based on a volume of the liquid (blood) determined from image information on the flat plate (disk 24 in this embodiment) storing the liquid (blood in this embodiment) and having a plurality of grooves and information on the grooves 26 grooved in the flat plate (disk 24), and two-dimensional image information on light or radiation (count information on radiation in this embodiment) obtained by the detecting device (imaging plate IP and reading unit 41), the information calculating device (information calculating unit 44) obtains information on light or radiation per unit volume (radioactive concentration in blood in this embodiment). That is, as for the liquid (blood) already transferred to the flat plate (disk 24), no variation such as a subsequent decrease occurs with the volume of the liquid (blood) derived from the image information on the flat plate (disk 24) and the information on the grooves 26 grooved in the flat plate (disk 24), and based on the volume of the liquid (blood), the information on light or radiation per unit volume (radioactive concentration in blood) is obtained. Therefore, by using the image information on the flat plate (disk 24), the information on light or radiation per unit volume (radioactive concentration in blood) can be obtained accurately, with no variation in the volume of the liquid (blood). The detecting device (imaging plate IP and reading unit 41) can reduce the influence of photobleaching of light or attenuation of radiation by carrying out simultaneous detection in two dimensions.

As noted above, description is made taking blood as an example of the liquid to be measured, and the imaging plate IP and reading unit 41 detect and count the radiation included in the blood. In this case, based on the volume of the blood and the count information on the radiation obtained by the imaging plate IP and reading unit 41, the information calculating device (information calculating unit 35 in this embodiment) can obtain count information on the radiation per unit volume (radioactive concentration in blood in this embodiment) accurately.

Where the liquid to be measured is blood as in this embodiment, the imaging plate IP and reading unit 41 count and detect separately, as two-dimensional radiation information, the radiation included in the plasma and blood cell resulting from a plasma separation centrifuging the blood. Based on the volume of each part of the plasma and blood cell and count information on the radiation of each part obtained by the imaging plate IP and reading unit 41, the information calculating device (information calculating unit 35 in this embodiment) obtains the count information on each part per unit volume (radioactive concentration in blood in this embodiment). It is possible to determine volumes of all parts of the plasma and blood cell on the disk 24 in parallel, thereby to obtain count information on each part per unit volume (radioactive concentration in blood in this embodiment) in parallel (i.e. to obtain at the same time). This simultaneous calculation can extend detection time (measuring time) by the imaging plate IP, which provides also an advantage that a low-concentration dose of radiation can be measured with high statistical accuracy.

With the blood collecting and measuring system according to this embodiment including the blood collecting apparatus 10 and measuring apparatus 40, as with the measuring apparatus 40 according to this embodiment, as for the liquid (blood in this embodiment) already transferred to the flat plate (disk 24), no variation such as a subsequent decrease occurs with the volume of the liquid (blood) derived from the image information on the flat plate (disk 24 in this embodiment) and the information on the grooves 26 grooved in the flat plate (disk 24), and based on the volume of the liquid (blood), the information on light or radiation per unit volume (radioactive concentration in blood in this embodiment) is obtained. Therefore, by using the image information on the flat plate (disk 24), the information on the light or the radiation per unit volume (radioactive concentration in blood) can be obtained accurately, with no variation in the volume of the liquid (blood).

In this embodiment, as described with relation to the blood collecting apparatus 10, the blood collecting and measuring system includes (a) a flow path (main flow path 13 in this embodiment) and (b) an extracting device (pressure generator 30 in this embodiment). Specifically, the extracting device (pressure generator 30) inserts, as separators at designated predetermined intervals, a gas (air, argon or the like in this embodiment) or a liquid (mineral oil, fluorine-based oil or the like where the liquid to be measured is blood) other than the above-noted liquid to be measured (blood in this embodiment), thereby to take out, as separated in a time series, the liquid (blood) to be measured. For each liquid (blood) taken out by the extracting device (pressure generator 30), the measuring apparatus 40 included in the system measures light generating from a luminescent or fluorescent substance included in the liquid (blood) or radiation included in the liquid (blood) to be measured (only radiation in this embodiment). Thus, as noted with relation to the blood collecting apparatus 10 according to this embodiment, the amount of collected liquid (the amount of collected blood) can be reduced, and the frequency of collection (blood collection) can be secured. As noted with relation to the measuring apparatus 40 according to this embodiment, the information on light or radiation per unit volume (radioactive concentration in blood in this embodiment) can be obtained accurately.

In the blood collecting and measuring system, as described with relation to the blood collecting apparatus 10, the above main flow path 13, preferably, is formed of what has been grooved in a predetermined size in the planar glass substrate 11. It is also preferred to include (c) an optical measuring device (light source 21 and photodiodes 22 in this embodiment). For application to centrifugal separation of the liquid (blood in this embodiment), (d) a flat plate (disk 24 in this embodiment) and (e) a rotating device (rotating unit 31 in this embodiment) are provided. The flat plate (disk 24) is the same as the flat plate which stores the liquid (blood) to be measured, and has a plurality of grooves formed in the predetermined size. The plurality of grooves are formed to allow the liquid (blood) to be measured to circulate with respect to the flow path (main flow path 13), and are formed to extend radially.

In carrying out such centrifugal separation, as noted with relation to the blood collecting apparatus 10 according to this invention, (f) an image pickup device (image pickup unit 32 in this embodiment), (g) a groove length and the groove area calculating device (groove length and groove area calculating 34 in this embodiment) and (h) a volume calculating device (volume calculating unit 35 in this embodiment) are provided. In this case, the shade difference of the image described with relation to the blood collecting apparatus 10 corresponds to the image information of the flat plate (disk 24 in this embodiment) in the blood collecting and measuring system. The cross-sectional area of grooves 26 or the depth of the grooves described with the blood collecting apparatus 10 corresponds to the information on the grooves in the blood collecting and measuring system.

In the blood collecting and measuring system, as described with relation to the measuring apparatus 40, blood is taken as an example of the liquid to be measured, and the imaging plate IP and reading unit 41 detect and count the radiation included in the blood. Where the liquid to be measured is blood as in this embodiment, as described with relation to the measuring apparatus 40 according to this embodiment, the imaging plate IP and reading unit 41 count and detect separately the radiation included in the plasma and blood cell resulting from the plasma separation centrifuging the blood. Based on the volume of each part of the plasma and blood cell and the count information on the radiation of each part obtained by the imaging plate IP and reading unit 41, the information calculating device (information calculating unit 35 in this embodiment) obtains the count information on each part per unit volume (radioactive concentration in blood in this embodiment).

This invention is not limited to the foregoing embodiment, but may be modified as follows:

(1) The foregoing embodiment is directed to the liquid collecting and measuring system (blood collecting and measuring system in the embodiment) including the liquid collecting apparatus (blood collecting apparatus 10 in the embodiment) and measuring apparatus (measuring apparatus 40 in the embodiment). Instead, the liquid collecting apparatus or measuring apparatus may be provided independently.

(2) In the foregoing embodiment, the liquid collecting apparatus (blood collecting apparatus 10 in the embodiment) has been described taking blood as an example of the liquid to be measured. The liquid to be measured is not limited to blood, but may be a liquid including a fluorescent agent or a mixed liquid for use in an analyzing apparatus, for example.

(3) In the foregoing embodiment, the liquid collecting apparatus (blood collecting apparatus 10 in the embodiment) includes (c) the optical measuring device (light source 21 and photodiodes 22 in the embodiment). However, it is not absolutely necessary to include the optical measuring device where the flow velocity is always constant. Although the light source 21 and photodiodes 22 have been described as an example of the optical measuring device, the light source 21 and photodiodes 22 are not limitative as long as the device measures the intervals of the liquid while optically monitoring the liquid to be measured. The light source 21 and photodiodes 22 are opposed to each other across the main flow path 13 as shown in FIG. 1, to constitute what is called the "transmission type sensor" for making detection based on light-shielding by the blood. Instead, what is called the "reflection type sensor" may be used to detect light reflected by the blood, with a light detecting device represented by photodiodes arranged at the same side as the light source.

(4) In the foregoing embodiment, the liquid collecting apparatus (blood collecting apparatus 10 in the embodiment) includes (d) the flat plate (disk 24 in this embodiment) and (e) the rotating device (rotating unit 31) for application to centrifugal separation of the liquid (blood in this embodiment). Where a centrifugal separation is not carried out, it is not absolutely necessary to include the flat plate or the rotating device. Each extract may be stored in the flat plate or a receptacle other than the flat plate from the dispenser 23 shown in FIG. 1. The flat plate may be a rectangular plate, a polygonal plate or the like without being limited to the disk 24 but, preferably, is shaped to have a rotation center at the center of gravity, considering that it is rotated. With the dispenser 23 interposed, the flat plate (disk 24) is formed to allow the liquid to be measured to circulate with respect to the flow path (main flow path 13 in the embodiment). The substrate (glass substrate 11 in the embodiment) may be constructed detachably attachable to the flat plate such that, when attached, the flow path (main flow path 13) and a groove 26 of flat plate fit together for allowing the liquid to be measured to circulate with respect to the flow path (main flow path 13 in the embodiment).

(5) In the foregoing embodiment, the liquid collecting apparatus (blood collecting apparatus 10 in the embodiment), where the centrifugal separation is carried out, includes (f) the image pickup device (image pickup unit 32 in the embodiment), (g) the groove length and the groove area calculating device (groove length and groove area calculating unit 34 in the embodiment) and (h) the volume calculating device (volume calculating unit 35 in the embodiment). When a quantitative analysis is conducted only with a taken-out volume, without determining a volume, it is not absolutely necessary to include the image pickup device, groove length and groove area calculating device or volume calculating device. Although the optical image pickup device such as the flat bed scanner has been described as an example of the image pickup device, this may be a radiation image pickup device formed of a radiation emitting device and a radiation detecting device. In the case of the radiation image pickup device, the parts of the centrifuged liquid are different from each other in radioactive concentration, and this different point is used. Particularly where the liquid is blood, the difference in radioactive concentration results in plasma and blood cell appearing as a shade difference on the image picked up, rendering them easily discernible on the image.

(6) In the foregoing embodiment, the measuring apparatus (measuring apparatus 40 in the embodiment) has been described taking blood as an example of the liquid to be measured, and the imaging plate IP and reading unit 41 detect and count radiation included in the blood. As noted in modification (2) above, it may be a liquid including a fluorescent agent. In the case of a liquid including a fluorescent agent, for example, a fluorescent substance which is the fluorescent agent is included in the liquid, and the measuring apparatus measures light generating from the fluorescent substance with a CCD camera or the like, to obtain information on light per unit volume accurately. In place of the imaging plate IP and reading unit 41, a two-dimensional radiation sensor (a scintillator array and a photomultiplier, or a semiconductor detector) may be used. Light generating from a luminescent substance may be measured similarly.

(7) In the foregoing embodiment, the blood collecting and measuring system includes (a) the flow path (main flow path 13 in the embodiment) and (b) the extracting device (pressure generator 30). There is no limitation as to the construction of the liquid collecting apparatus (blood collecting apparatus 10 in the embodiment) included in the system, as long as the liquid to be measured is collected. It is not absolutely necessary to include the flow path or the extracting device. Quantitative analysis may be conducted using a liquid collected in a receptacle for samples. The same applies to the measuring apparatus 40.

The invention claimed is:

1. A measuring apparatus for measuring light generating from a luminescent or fluorescent substance included in a liquid to be measured or radiation included in the liquid to be measured, comprising (A) a detecting device for simultaneously detecting the light or the radiation in two dimensions to obtain two-dimensional image information on the light or the radiation, and (B) an information calculating device for obtaining information on the light or the radiation per unit volume based on a volume of the liquid determined from image information on a flat plate storing the liquid and having a plurality of grooves and information on the grooves grooved in the flat plate, and the two-dimensional image information on the light or the radiation obtained by the detecting device.

2. The measuring apparatus according to claim 1, wherein the liquid to be measured is blood, the detecting device counts by detecting the radiation included in the blood, and the information calculating device obtains count information on the radiation per unit volume based on a volume of the blood and count information on the radiation obtained by the detecting device.

3. The measuring apparatus according to claim 2, wherein the detecting device counts by separately detecting the radiation included in plasma and blood cell resulting from a plasma separation centrifuging the blood, and the information calculating device obtains count information on each part per unit volume based on a volume of each part of the blood and blood cell and the count information on the radiation of each part obtained by the detecting device.

4. A liquid collecting and measuring system having a liquid collecting apparatus for collecting a liquid to be measured, and a measuring apparatus for measuring light generating from a luminescent or fluorescent substance included in the liquid collected or radiation included in the liquid, comprising (A) a detecting device for simultaneously detecting the light or the radiation in two dimensions to obtain two-dimensional image information on the light or the radiation, and (B) an information calculating device for obtaining information on the light or the radiation per unit volume based on a volume of the liquid determined from image information on a flat plate storing the liquid and having a plurality of grooves and information on the grooves grooved in the flat plate, and the two-dimensional image information on the light or the radiation obtained by the detecting device.

5. The liquid collecting and measuring system according to claim 4, wherein the liquid collecting apparatus includes (a) a flow path through which the liquid to be measured flows, and (b) an extracting device provided in an intermediate position of the flow path to insert a gas or a liquid other than the liquid to be measured, as separators, at designated predetermined intervals, thereby to take out the liquid to be measured, as separated in a time series, and wherein, for each liquid taken out by the extracting device, the measuring apparatus measures light generating from a luminescent or fluorescent substance included in the liquid or radiation included in the liquid to be measured.

6. The liquid collecting and measuring system according to claim 5, wherein the flow path is formed of what has been grooved in a predetermined size in a planar substrate.

7. The liquid collecting and measuring system according to claim 5, wherein the liquid collecting apparatus includes (c) an optical measuring device for measuring length information on the liquid while optically monitoring the liquid to be measured flowing through the flow path, wherein a volume of the liquid to be taken out by the extracting device is controlled by controlling the intervals of the separators based on a result of measurement by the optical measuring device.

8. The liquid collecting and measuring system according to claim 5, wherein the liquid collecting apparatus includes (d) a flat plate having a plurality of grooves formed to allow the liquid to be measured to circulate with respect to the flow path and formed radially, and (e) a rotating device for rotating the flat plate, wherein the liquid is centrifuged using a centrifugal force of the flat plate by the rotating device.

9. The liquid collecting and measuring system according to claim 8, wherein the liquid collecting apparatus includes (f) an image pickup device for picking up an image of the flat plate, (g) a groove length and groove area calculating device for determining a groove length or a groove area of each part of the centrifuged liquid based on the image information of the flat plate which is a shade difference of the image picked up by the image pickup device of the grooves grooved in the flat plate, and (h) a volume calculating device for determining a volume of each part based on the information on the grooves which is the groove length of each part of the liquid determined by the groove length and groove area calculating device and a cross-sectional area of the grooves, or based on the information on the grooves which is the groove area of each part of the liquid determined by the groove length and groove area calculating device and a depth of the grooves, and wherein the information calculating device obtains information on the light or the radiation per unit volume based on the volume of the liquid determined by the volume calculating device and the two-dimensional image information on the light or the radiation obtained by the detecting device.

10. The liquid collecting and measuring system according to claim 4, wherein the liquid to be measured is blood, and the liquid collecting apparatus is an apparatus for collecting the blood, and wherein the detecting device counts by detecting the radiation included in the blood, and the information calculating device obtains count information on the radiation per unit volume based on a volume of the blood and count information on the radiation obtained by the detecting device.

11. The liquid collecting and measuring system according to claim 10, wherein the detecting device counts by separately detecting the radiation included in plasma and blood cell resulting from a plasma separation centrifuging the blood, and the information calculating device obtains count information on each part per unit volume based on a volume of each part of the blood and blood cell and the count information on the radiation of each part obtained by the detecting device.

\* \* \* \* \*